(12) United States Patent
Jasper et al.

(10) Patent No.: US 10,099,975 B2
(45) Date of Patent: *Oct. 16, 2018

(54) ALKYNYL-TOLANES, LIQUID-CRYSTAL MIXTURES CONTAINING THEM AND COMPONENTS FOR HIGH-FREQUENCY TECHNOLOGY

(71) Applicant: MERCK PATENT GMBH, Darmstadt (DE)

(72) Inventors: Christian Jasper, Seligenstadt (DE); Constanze Brocke, Gross-Gerau (DE); Detlef Pauluth, Ober-Ramstadt (DE); Volker Reiffenrath, Rossdorf (DE); Atsutaka Manabe, Bensheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/913,807

(22) PCT Filed: Aug. 11, 2014

(86) PCT No.: PCT/EP2014/002194
§ 371 (c)(1),
(2) Date: Feb. 23, 2016

(87) PCT Pub. No.: WO2015/024635
PCT Pub. Date: Feb. 26, 2015

(65) Prior Publication Data
US 2016/0208167 A1 Jul. 21, 2016

(30) Foreign Application Priority Data
Aug. 23, 2013 (EP) .................... 13004178

(51) Int. Cl.
| | | |
|---|---|---|
| *C07C 15/18* | (2006.01) |
| *C07C 13/47* | (2006.01) |
| *C07C 13/573* | (2006.01) |
| *C07C 15/24* | (2006.01) |
| *C07C 25/24* | (2006.01) |
| *C07D 213/24* | (2006.01) |
| *C07D 307/36* | (2006.01) |
| *C07D 307/38* | (2006.01) |
| *C07D 333/10* | (2006.01) |
| *C07D 333/12* | (2006.01) |
| *C09K 19/18* | (2006.01) |
| *C09K 19/32* | (2006.01) |
| *C09K 19/34* | (2006.01) |

(52) U.S. Cl.
CPC ............. *C07C 15/18* (2013.01); *C07C 13/47* (2013.01); *C07C 13/573* (2013.01); *C07C 15/24* (2013.01); *C07C 25/24* (2013.01); *C07D 213/24* (2013.01); *C07D 307/36* (2013.01); *C07D 307/38* (2013.01); *C07D 333/10* (2013.01); *C07D 333/12* (2013.01); *C09K 19/18* (2013.01); *C09K 19/32* (2013.01); *C09K 19/322* (2013.01); *C09K 19/3405* (2013.01); *C09K 19/3444* (2013.01); *C09K 19/3447* (2013.01); *C09K 19/3491* (2013.01); *C09K 2019/181* (2013.01); *C09K 2219/11* (2013.01)

(58) Field of Classification Search
CPC ....... C07C 13/47; C07C 13/573; C07C 15/18; C07D 213/24; C07D 307/36; C07D 307/38; C07D 333/10; C07D 333/12; C09K 19/3444; C09K 19/3447; C09K 19/3059; C09K 19/18; C09K 19/32; C09K 19/3491
See application file for complete search history.

(56) References Cited

U.S. PATENT DOCUMENTS

| | | | | |
|---|---|---|---|---|
| 5,154,851 A | | 10/1992 | Goto et al. | |
| 5,626,792 A | * | 5/1997 | Wand .................. | C09K 19/0225 252/299.01 |
| 5,658,489 A | * | 8/1997 | Higashii ................ | C09K 19/18 252/299.01 |
| 5,986,096 A | * | 11/1999 | Lewis ................... | C07D 239/28 252/299.62 |
| 6,149,837 A | * | 11/2000 | Sekine .................. | C07C 255/50 252/299.01 |

(Continued)

FOREIGN PATENT DOCUMENTS

| | | | |
|---|---|---|---|
| CN | 1927856 A | * | 3/2007 |
| CN | 100569716 C | | 12/2009 |

(Continued)

OTHER PUBLICATIONS

English Translation of CN1927856.*

(Continued)

*Primary Examiner* — Cynthia H Kelly
*Assistant Examiner* — Anna Malloy
(74) *Attorney, Agent, or Firm* — Millen White Zelano and Branigan, PC; Csaba Henter

(57) ABSTRACT

Compounds of formula I

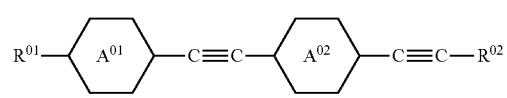

their use in liquid-crystalline media, for example, for the phase shifting of microwaves for tunable phased-array antennae, and their use for high-frequency components, in particular antennae, especially for the gigahertz range.

22 Claims, No Drawings

(56) References Cited

U.S. PATENT DOCUMENTS

| | | | |
|---|---|---|---|
| 7,255,811 B2* | 8/2007 | Hirschmann | C07C 17/269 252/299.01 |
| 7,846,514 B2 | 12/2010 | Shimada et al. | |
| 8,999,198 B2 | 4/2015 | Reiffenrath et al. | |
| 2003/0011725 A1* | 1/2003 | Ohkawa | C09K 19/18 349/96 |
| 2004/0236138 A1 | 11/2004 | Hirschmann et al. | |
| 2010/0073621 A1* | 3/2010 | Shimada | C09K 19/10 349/182 |
| 2013/0221274 A1 | 8/2013 | Reiffenrath et al. | |
| 2014/0008575 A1* | 1/2014 | Jasper | C09K 19/18 252/299.66 |
| 2014/0217325 A1* | 8/2014 | Manabe | C07C 15/54 252/299.63 |

FOREIGN PATENT DOCUMENTS

| | | | | |
|---|---|---|---|---|
| CN | 101616883 A | 12/2009 | | |
| DE | 102011112950 A1 | 4/2012 | | |
| EP | 0377516 A2 | 7/1990 | | |
| EP | 0648723 A1 | 5/1998 | | |
| JP | 06298686 A | * 10/1994 | | |
| TW | 201247850 A | 12/2012 | | |
| WO | WO 2012126563 A1 * | 9/2012 | | C09K 19/18 |
| WO | 2013034227 A1 | 3/2013 | | |

OTHER PUBLICATIONS

English Translation of JP06298686.*
Piskunov et al., "Synthesis of 9,10-diacetylenylanthracenes", Jun. 1990, Institute of Chemical Kinetics and Combustion, Siberian Branch, Academy of Sciences of the USSR, Novosibirsk. Kemero State University. Translated from Izvestiya Akademii Nauk SSSR, Seriya Khimicheskaya, No. 6, 1441-1443.*
Lind et al., "Structural, Photophysical, and Nonlinear Absorption Properties of trans-Di-arylalkynyl Platinum(II) Complexes with Phenyl and Thiophenyl Groups", Feb. 10, 2007, Journal of Physical Chemistry A, 111, 1598-1609.*
Jones et al., "Rapid Solution and Solid Phase Syntheses of Oligo(1,4-phenylene ethynylene)s with Thioester Termini: Molecular Scale Wires with Alligator Clips. Derivation of Iterative Reaction Efficiencies on a Polymer Support", Journal of Organic Chemistry, 1997, 62, 1388-1410.*
Muhling et al., "Push-Pull-Substituted Oligo(2,5-thienyleneethynylene)s", 2006, Synthesis, No. 6, 1009-1015.*
Cramer et al., "Oligo(naphthylene-ethynylene) Molecular Rods", Mar. 19, 2013, European Jorunal of Organic Chemistry, 2813-2822.*
Yatabe et al., "Liquid crystalline alkyl-substituted oligo(p-phenyleneethynylene )s: synthesis and structure-property relationships", Mar. 2012, Liquid Crystals, vol. 39 No. 3, 269-284.*
Yuan et al., "First-Principles Study of Rectification in Bis-2-(5-ethynylthienyl)ethyne Molecular Junctions", 2011, Journal of Physical Chemistry A, 115, 9033-9042.*
Pertici et al., "Efficient synthesis of phenylene-ethynylene rods and their use as rigid spacers in divalent inhibitors", Jan. 31, 2013, Beilstein Journal of Organic Chemistry, 9, 215-222.*
International Search Report for PCT/EP2014/002194 dated Oct. 17, 2014.
Office Action for related Chinese Patent Application No. 201480046608.6 dated Oct. 25, 2017.

* cited by examiner

ALKYNYL-TOLANES, LIQUID-CRYSTAL MIXTURES CONTAINING THEM AND COMPONENTS FOR HIGH-FREQUENCY TECHNOLOGY

The present invention relates to alkynyltolans, to liquid-crystalline media comprising these compounds, to the use thereof for high-frequency components, and to high-frequency components, in particular antennae and phase shifters, especially for the gigahertz and terahertz range, comprising these media. The liquid-crystalline media serve, for example, for the phase shifting of microwaves for tunable 'phased-array' antennae.

Liquid-crystalline media have been used for some time in electro-optical displays (liquid crystal displays—LCDs) in order to display information.

However, liquid-crystalline media have recently also increasingly been proposed for use in components for high-frequency technology, in particular microwave technology, such as, for example, in DE 10 2004 029 429 A and in JP 2005-120208 (A).

An industrially valuable application of liquid-crystalline media in high-frequency technology is based on their property that their dielectric properties can be controlled by a variable voltage, particularly for the gigahertz region. Thus, tuneable antennae can be designed which contain no moving parts (A. Gaebler, A. Moessinger, F. Goelden, et al., "Liquid Crystal-Reconfigurable Antenna Concepts for Space Applications at Microwave and Millimeter Waves", International Journal of Anntenae and Propagation, Vol. 2009, Article ID 876989, 7 pages, 2009. doi:10.1155/2009/876989).

The publication A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, 545-548, describes, inter alia, the properties of the known, liquid-crystalline single substance K15 (Merck KGaA, Germany) at a frequency of 9 GHz.

DE 10 2004 029 429 A (cf. above) describes the use of conventional liquid-crystal media in microwave technology, inter alia in phase shifters. Liquid-crystalline media have already been investigated therein with respect to their properties in the corresponding frequency range.

Compounds containing a C—C triple bond within a chain of 4 benzene rings arranged in a linear manner are disclosed in the specifications JP 05-255151 A and WO 2009/125721 A1. Some of the compounds from JP 05-255151 A are provided with fluorine substituents and are used as a component of liquid-crystalline media. The compounds disclosed in the second specification are only substituted at the ends of the molecule and serve as a constituent of thin-film transistors.

Liquid-crystalline compounds having very high optical anisotropy and clearly positive values of the dielectric anisotropy are rare to date. Compounds of this type are certain bistolans containing a polar end group, as disclosed, for example, in the publications Shin-Tson Wu et al. Jpn. J. Appl. Phys. 1999, 38, 286-288, Shin-Tson Wu et al. Jpn. J. Appl. Phys. 2000, 39, 38-41, JP 10-45642 A and DE10120024.

However, the compositions or individual compounds known to date are generally afflicted with disadvantages. Most of them result, besides other deficiencies, in disadvantageously high losses and/or inadequate phase shifts or inadequate material quality. Whereas, for example, some individual compounds do not have favourable liquid-crystalline phases and have very high melting points, other substances in turn lack sufficiently high values of $\Delta n$ and $\Delta \varepsilon$.

For use in high-frequency technology, liquid-crystalline media having particular, to date rather unusual, non-standard properties, or combinations of properties, are required.

Thus, novel components for liquid-crystalline media having improved properties are necessary. In particular, the loss in the microwave range must be reduced and the material quality (η) must be improved. Furthermore, applications in antenna technology take place under in some cases strongly varying outside boundary conditions, such as, for example, large temperature variations. In particular, there is a need to improve the low-temperature behaviour of the components.

There is therefore a considerable demand for liquid-crystalline media having suitable properties for corresponding practical applications.

Compounds of the formula

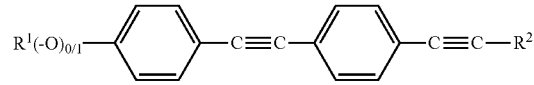

in which $R^1$ and $R^2$ denote alkyl are disclosed in EP 0 377 516 (A).

The compound of the formula

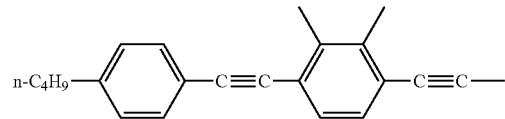

is known from DE 10 2011 112 950 A1.

Surprisingly, it has been found that the compounds according to the invention have low melting points and high clearing points (transition from the nematic phase into the isotropic phase). In the liquid-crystalline range, the compounds are predominantly nematic or support the nematic phase. At the same time, the optical anisotropy ($\Delta n$) and the dielectric anisotropy ($\Delta \varepsilon$) equally have high positive values, making them highly suitable, for example, for use as high-frequency medium. In addition, the compounds have low viscosities in particular low rotational viscosities. This is particularly important in some applications in which the response times are important. It has now been found that, with the compounds according to the invention, it is possible to achieve liquid-crystalline media having a broad nematic phase range and at the same time high values for $\Delta n$ and $\Delta \varepsilon$, and advantageous high-frequency properties.

The invention relates to compounds of the formula I,

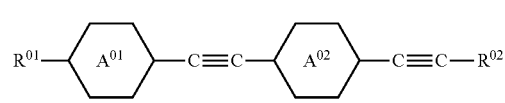

in which

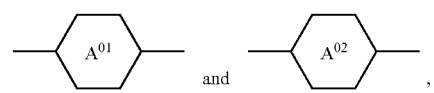

independently of one another, denote

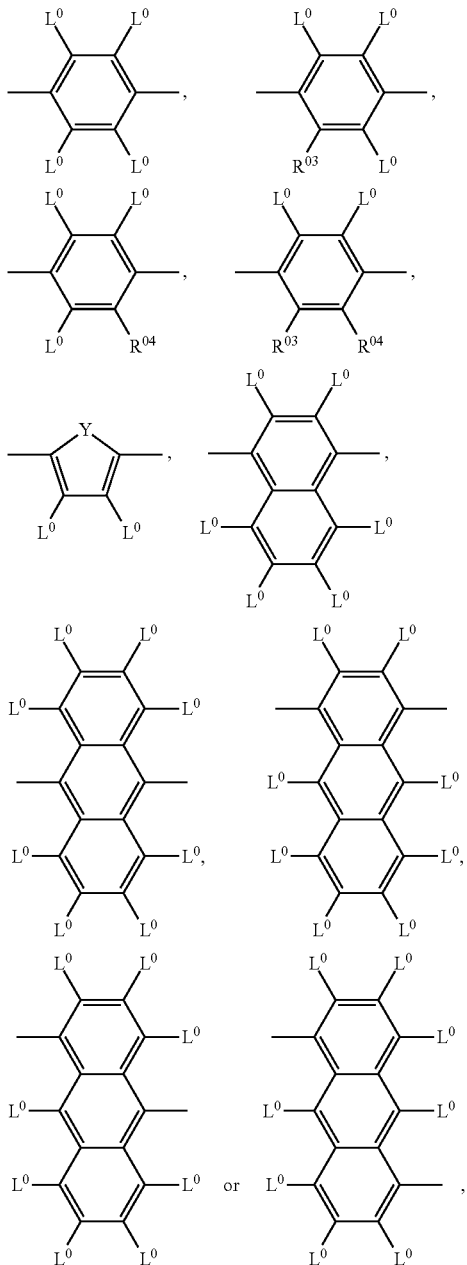

preferably

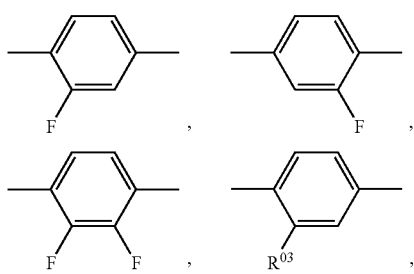

particularly preferably

[structures with $R^{03}$, $R^{04}$]

in which Y denotes S or O, where only one of

[ring with $A^{01}$] and [ring with $A^{02}$] can denote

[phenylene ring], and where in the 1,4-phenylene groups, one C—H group or a plurality of C—H groups, preferably one C—H group or two C—H groups, preferably not adjacent, particularly preferably one C—H group, may be replaced by N, and $L^0$ on each occurrence, independently of one another, denotes H, Br, Cl, F, —CN, —NCS, —SCN, $SF_5$, $C_1$-$C_{10}$ alkyl, $C_1$-$C_{10}$ alkoxy, $C_3$-$C_6$ cycloalkyl or a mono- or polyfluorinated $C_1$-$C_{10}$ alkyl or alkoxy group, $R^{01}$ and $R^{02}$ each, independently of one another, denote a halogenated or unsubstituted alkyl radical having 1 to 15 C atoms, where, in addition, one or more $CH_2$ groups in these radicals may each be replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another and, optionally, independently of one another, $R^{01}$ may also denote ethynyl (i.e. —C≡CH) and $R^{02}$ may also denote H, and $R^{03}$ and $R^{04}$ each, independently of one another, denote a halogenated or unsubstituted alkyl radical having 1 to 6, preferably having 1 to 4, particularly preferably having 1, 2 or 3, C atoms, where, in addition, one or more $CH_2$ groups in these radicals may each be replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another, where, in the case where

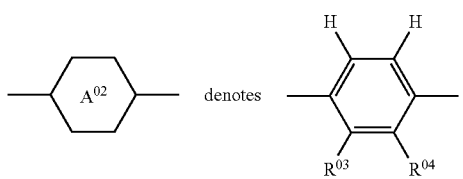

and
$R^{03}$ and $R^{04}$ both denote $CH_3$,
$R^{01}$ denotes alk-1-ynyl.

The double bonds of the sub-formula —CH=CH—, —CH=CF—, —CF=CH— or —CF=CF— in the corresponding groups preferably have the trans-configuration (E-configuration).

The compounds according to the invention have a comparatively very low melting point, a high clearing point, high optical anisotropy (Δn) and clearly positive dielectric anisotropy. The undesired rotation of the compounds is restricted, making them particularly suitable for use in the gigahertz region. The relatively low loss factor in the microwave spectrum is advantageous. The compounds have, alone or in a mixture with further mesogenic components, a nematic phase over a broad temperature range. The totality of these properties make them particularly suitable for use in components for high-frequency technology, in particular in liquid-crystalline phase shifters. Liquid-crystalline media according to the invention have the corresponding properties.

Preferred compounds of the formula I are characterised by the choice of one or more of the following parameters:

Particularly preferred moieties "-$A^{01}$-≡-$A^{02}$-" here are selected from the following moieties:

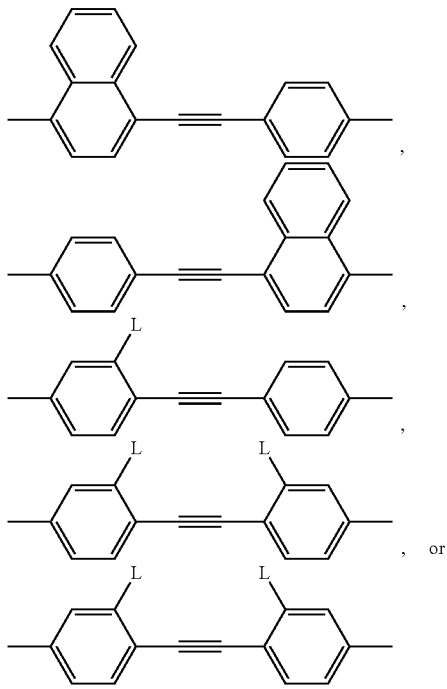

$R^{01}$ preferably denotes a straight-chain alkyl radical having 1 to 15 C atoms or an alkynyl radical, preferably an alk-1-ynyl radical, having 2 to 15 C atoms, where, in addition, one or more $CH_2$ groups in these radicals may each be replaced, independently of one another, by —C≡C—, —CH=CH—, —(CO)O—, —O(CO)—, —(CO)—, —O— in such a way that O atoms are not linked directly to one another. The group $R^{01}$ is preferably an alkyl radical having 2 to 7 C atoms.

The group L preferably denotes methyl, ethyl, propyl, cyclopropyl or Cl.

Preferred embodiments of the invention are therefore represented by the following illustrative structures:

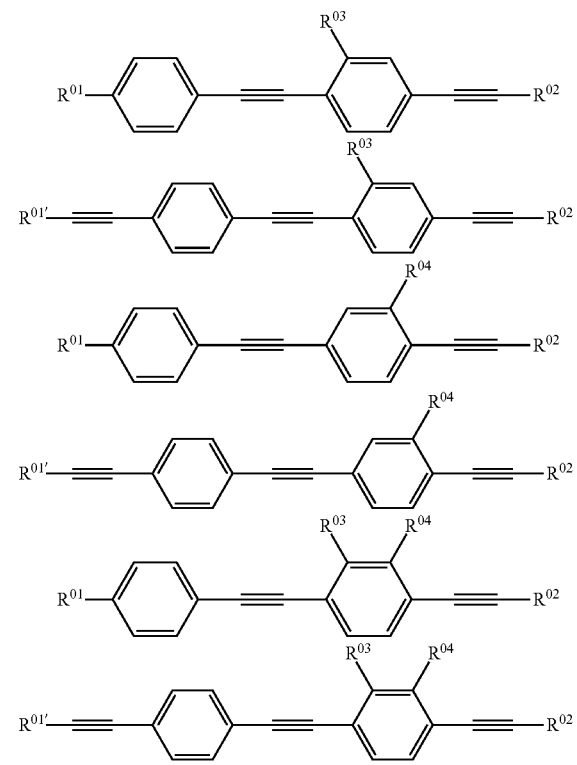

in which $R^{01}$ to $R^{04}$ are as defined in formula I, and in particular $R^{01}$ and $R^{01'}$ denote an alkyl radical having 1 to 7 C atoms in the case of $R^{01}$, and 1 to 5 C atoms in the case of $R^{01'}$, for example a methyl, ethyl, propyl, butyl, pentyl or hexyl radical, $R^{02}$ denotes an alkyl radical having 1 to 7 C atoms, for example a methyl, propyl, butyl, pentyl or hexyl radical, $R^{03}$ denotes an alkyl radical having 1 to 7 C atoms, preferably a methyl, ethyl or propyl radical, and $R^{04}$ denotes an alkyl radical having 1 to 7 C atoms, preferably a methyl, ethyl or propyl radical.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

Typical compounds of the formula I can advantageously be prepared as evident from the following illustrative synthesis schemes (Schemes 1 to 5):

Scheme 1: Preparation of compounds of the formula I, in which, as in the other schemes, the parameters have the respective meanings given above.

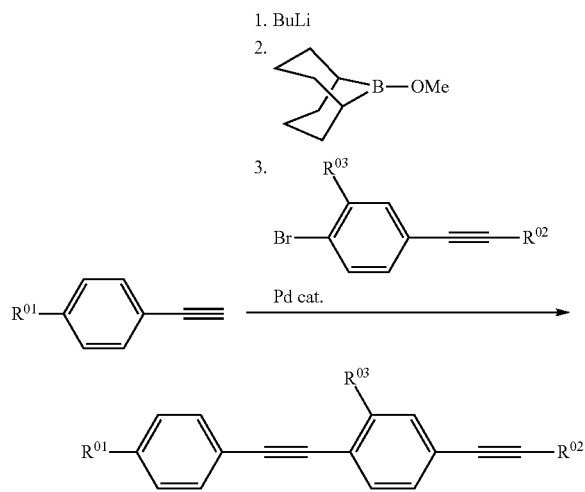

Scheme 2: Preparation of compounds of the formula I.

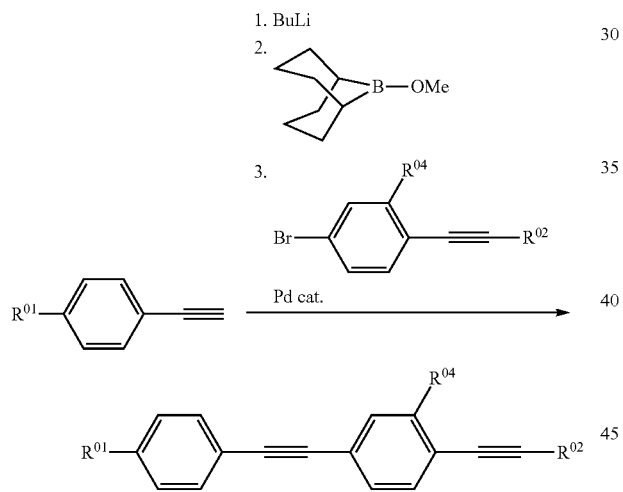

Scheme 3: Preparation of compounds of the formula I.

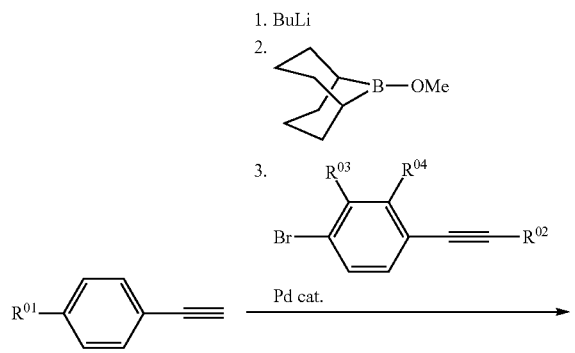

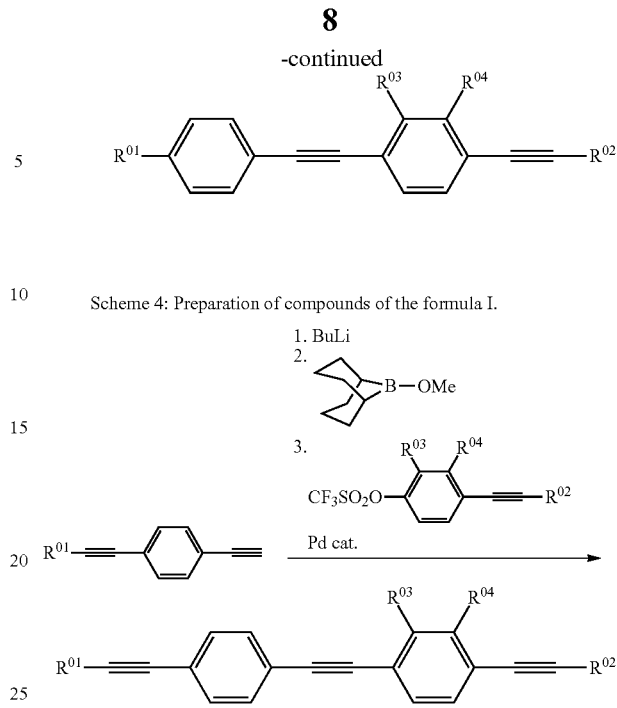

Scheme 4: Preparation of compounds of the formula I.

Scheme 5: Preparation of compounds of the formula I in which the ring A02 denotes 1,4-naphthylene.

$R^{01}$ to $R^{04}$ in Schemes 1 to 5 have the meaning as defined for formula I. In Reaction Schemes 1 to 5, the synthesis of compounds of the formula I is reproduced with certain, preferred embodiments. The phenylene radicals and naphthylene radicals may optionally be substituted.

The parameters are as defined above and below.

The liquid-crystalline media in accordance with the present invention comprise one or more compounds of the formula I and optionally at least one further, preferably mesogenic compound. The liquid-crystal medium therefore preferably comprises two or more compounds which are preferably liquid-crystalline. Preferred media comprise the preferred compounds of the formula I.

Further components of the liquid-crystalline media are preferably selected from the compounds of the formula II:

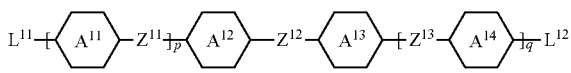

II in which
L$^{11}$ denotes R$^{11}$ or X$^{11}$,
L$^{12}$ denotes R$^{12}$ or X$^{12}$,
R$^{11}$ and R$^{12}$, independently of one another, denote unfluorinated alkyl or unfluorinated alkoxy having 1 to 17, preferably having 3 to 10, C atoms or unfluorinated alkenyl, unfluorinated alkynyl, unfluorinated alkenyloxy or unfluorinated alkoxyalkyl having 2 to 15, preferably 3 to 10, C atoms, preferably alkyl or unfluorinated alkenyl,
X$^{11}$ and X$^{12}$, independently of one another, denote F, Cl, Br, —CN, —NCS, —SCN, SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl,
p, q, independently of one another, denote 0 or 1,
Z$^{11}$ to Z$^{13}$, independently of one another, denote trans-CH=CH—, trans-CF=CF—, —C≡C— or a single bond,

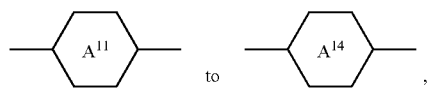

independently of one another, denote

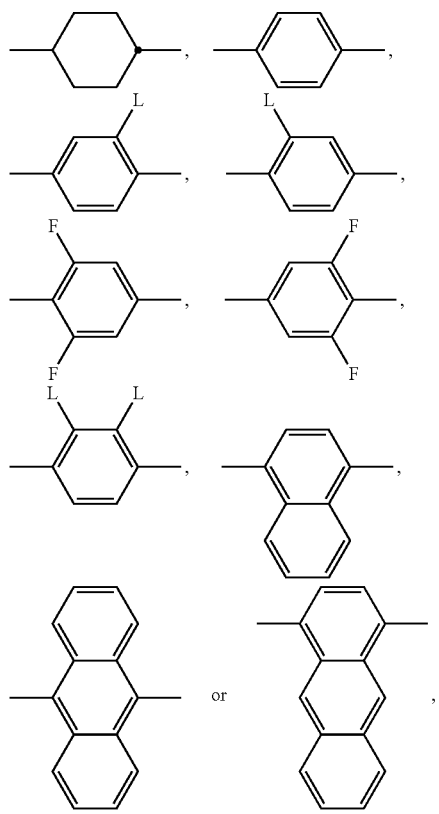

and
L on each occurrence, independently of one another, denotes branched or unbranched alkyl, alkenyl or alkynyl having 1 to 12 C atoms, in which, independently of one another, one or more "—CH$_2$—" groups may also be replaced by O, or denotes C$_3$-C$_6$ cycloalkyl, C$_3$-C$_6$ cycloalkenyl, fluorinated alkyl or alkenyl, fluorinated alkoxy or alkenyloxy, F, Cl, Br, CN, NCS, SCN or SF$_5$.

In a preferred embodiment of the present invention, the liquid-crystalline media comprise one or more compounds of the formula I and one or more compounds of the formula II.

The liquid-crystalline media in accordance with the present application preferably comprise in total 5 to 95%, preferably 10 to 90% and particularly preferably 15 to 80%, of compounds of the formula I.

The liquid-crystalline media in accordance with the present invention preferably comprise, more preferably predominantly consist of, even more preferably essentially consist of and very preferably completely consist of compounds selected from the group of the compounds of the formulae I and II.

In this application, "comprise" in connection with compositions means that the entity in question, i.e. the medium or the component, comprises the component or components or compound or compounds indicated, preferably in a total concentration of 10% or more and very preferably 20% or more.

In this connection, "predominantly consist of" means that the entity in question comprises 55% or more, preferably 60% or more and very preferably 70% or more, of the component or components or compound or compounds indicated.

In this connection, "essentially consist of" means that the entity in question comprises 80% or more, preferably 90% or more and very preferably 95% or more, of the component or components or compound or compounds indicated.

In this connection, "completely consist of" means that the entity in question comprises 98% or more, preferably 99% or more and very preferably 100.0%, of the component or components or compound or compounds indicated.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants and nanoparticles. The individual, added compounds are employed in concentrations of 0.005 to 6%, preferably 0.1 to 3%. The total concentration of these further constituents is in the range from 0% to 10%, preferably 0.1% to 6%, based on the mixture as a whole. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethyl-piperidines or 2-benzotriazol-2-ylphenols. These assistants are known to the person skilled in the art and are commercially available, for example as light stabilisers.

An embodiment of the invention is therefore also a process for the preparation of a liquid-crystal medium which is characterised in that one or more compounds of the formula I are mixed with one or more further compounds and optionally with one or more additives. The further compounds are preferably selected from the compounds of the formula II, as indicated above, and optionally one or more further compounds.

In the present application, the expression dielectrically positive describes compounds or components where $\Delta\epsilon>3.0$, dielectrically neutral describes those where $-1.5 \leq \Delta\epsilon \leq 3.0$ and dielectrically negative describes those where $\Delta\epsilon<-1.5$. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

$\Delta\epsilon$ is defined as $(\epsilon_{\parallel}-\epsilon_{\perp})$, while $\epsilon_{average}$ is $(\epsilon_{\parallel}+2\epsilon_{\perp})/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The term threshold voltage in the present application refers to the optical threshold and is quoted for 10% relative contrast ($V_{10}$), and the term saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties that are typical for liquid crystals are determined in accordance with "Merck Liquid Crystals, Physical Properties of Liquid Crystals", status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\epsilon$) is determined at a frequency of 1 kHz. The threshold voltages, as well as all other electro-optical properties, are determined using test cells produced at Merck KGaA, Germany. The test cells for the determination of $\Delta\epsilon$ have a cell thickness of approximately 20 μm. The electrode is a circular ITO electrode having an area of 1.13 cm$^2$ and a guard ring. The orientation layers are SE-1211 from Nissan Chemicals, Japan, for homeotropic orientation ($\epsilon_{\parallel}$) and polyimide AL-1054 from Japan Synthetic Rubber, Japan, for homogeneous orientation ($\epsilon_{\perp}$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages are determined under perpendicular observation. The threshold ($V_{10}$), mid-grey ($V_{50}$) and saturation ($V_{90}$) voltages are determined for 10%, 50% and 90% relative contrast respectively.

The liquid-crystalline media are investigated with respect to their properties in the microwave frequency range as described in A. Penirschke et al. "Cavity Perturbation Method for Characterization of Liquid Crystals up to 35 GHz", 34$^{th}$ European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an internal radius of 180 μm and an external radius of 350 The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the result of the output signal is recorded using a commercial vector network analyser. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

The dielectric anisotropy in the microwave region is defined as $$\Delta\epsilon_r \equiv (\epsilon_{r,\parallel}-\epsilon_{r,\perp}).$$

The modulatability or tunability ($\tau$) is defined as $$\tau \equiv (\Delta\epsilon_r/\epsilon_{r,\parallel}).$$

The material quality ($\eta$) is defined as $$\eta \equiv (\tau/\tan\delta_{\epsilon_r,max.})$$

with the maximum dielectric loss factor $\tan\delta_{\epsilon_r,max.}$:

$$\tan\delta_{\epsilon_r,max.} \equiv \max.\{\tan\delta_{\epsilon_r,\perp}; \tan\delta_{\epsilon_r,\parallel}\}$$

which arises from the maximum value of the measured values for tan $\delta_{\in,r}$.

The material quality ($\eta$) of the preferred liquid-crystal materials is 6 or more, preferably 7 or more, preferably 10 or more, preferably 15 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 180° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a cell thickness of 5 µm for at least 100 hours. At high temperatures, the clearing point is measured in capillaries by conventional methods.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The $\Delta\in$ of the liquid-crystal medium in accordance with the invention, at 1 kHz and 20° C., is preferably 1 or more, more preferably 2 or more and very preferably 3 or more.

The $\Delta n$ of the liquid-crystal media in accordance with the present invention, at 589 nm ($Na^D$) and 20° C., is preferably in the range from 0.20 or more to 0.90 or less, more preferably in the range from 0.25 or more to 0.90 or less, even more preferably in the range from 0.30 or more to 0.85 or less and very particularly preferably in the range from 0.35 or more to 0.80 or less.

In a preferred embodiment of the present application, the $\Delta n$ of the liquid-crystal media in accordance with the present invention is preferably 0.50 or more, more preferably 0.55 or more.

Furthermore, the liquid-crystal media according to the invention are characterised by high anisotropies in the microwave region. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

The liquid crystals employed are either single substances or mixtures. They preferably have a nematic phase.

In the present application, the term compounds means both one compound and a plurality of compounds, unless expressly stated otherwise.

Preferred components which comprise a liquid-crystal medium or at least one compound in accordance with the invention are phase shifters, varactors, antenna arrays (for example for radio, mobile communications, microwave/radar and other data transmission), 'matching circuit adaptive filters' and others. Preference is given to components for high-frequency technology, as defined above. Preference is also given to components which can be modulated by different applied electrical voltages. Very particularly preferred components are tuneable phase shifters. In preferred embodiments, a plurality of phase shifters are functionally connected, giving, for example, a phase-controlled group antenna, generally referred to as 'phased array' antenna. A group antenna uses the phase shift of the transmitting or receiving elements arranged in a matrix in order to achieve bundling through interference. A parallel arrangement of phase shifters in row or grid form enables the construction of a so-called 'phased array', which can serve as tuneable or passive transmitting or receiving antenna for high frequencies (for example gigahertz region). Phased-array antennae according to the invention have a very broad usable reception cone.

Preferred applications are radar installations and data transmission equipment on manned or unmanned vehicles from the automobile, shipping, aircraft, space travel and satellite technology areas.

For the production of suitable components for high-frequency technology, in particular suitable phase shifters, a liquid-crystalline medium according to the invention is typically introduced into rectangular cavities having a thickness of less than 1 mm, a width of several millimeters and a length of several centimeters. The cavities have opposing electrodes mounted along two long sides. Such arrangements are familiar to the person skilled in the art. Through application of a variable voltage, the dielectric properties of the liquid-crystalline medium can be tuned during operation of the antenna in order to set different frequencies or directions of an antenna.

The expression "halogen" or "halogenated" stands for F, Cl, Br and I, particularly for F and Cl and in particular for F. A halogenated alkyl radical therefore preferably means a chlorinated or fluorinated alkyl radical.

The expression "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The expression "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The expression "alkoxy" preferably encompasses straight-chain radicals of the formula $C_nH_{2n+1}$—O—, in which n denotes 1 to 10. n is preferably 1 to 6. Preferred alkoxy groups are, for example, methoxy, ethoxy, n-propoxy, n-butoxy, n-pentoxy, n-hexoxy, n-heptoxy, n-octoxy, n-nonoxy, n-decoxy.

The expression "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

The expression "fluorinated alkyl radical" preferably encompasses mono- or polyfluorinated radicals. Perfluorinated radicals are included. Preference is given to $CF_3$, $CH_2CF_3$, $CH_2CHF_2$, $CHF_2$, $CH_2F$, $CHFCF_3$ and $CF_2CHFCF_3$, particularly preferably $CF_3$.

The expression "fluorinated alkoxy radical" encompasses mono- or polyfluorinated radicals. Perfluorinated radicals are preferred. Particular preference is given to the $OCF_3$ radical.

The expression "alk(en/yn)yl groups, in which one or more "—$CH_2$—" groups may be replaced by —O—" preferably relates to groups of this type in which a non-terminal $CH_2$ group is replaced. OH groups are included in the general meaning.

The expression "substituted cycloalkyl" encompasses cycloalkyl which is mono- or polysubstituted by alkyl, in particular alkyl having 1 to 8 carbon atoms.

The expression "substituted phenyl" encompasses phenyl which is mono- or polysubstituted by a group defined like $R^1$, in particular phenyl which is substituted by F, Cl, alkyl or alkoxy.

In the present application, high-frequency technology means applications having frequencies in the range from 1 MHz to 10 THz, preferably from 1 GHz to 3 THz, more preferably from 2 GHz to 1 THz, particularly preferably from 5 to 300 GHz. The application is preferably in the microwave spectrum or adjacent regions which are suitable for message transmission, in which phased-array modules can be used in transmitting or receiving antennae.

The liquid-crystal media according to the invention consist of one or more compounds, preferably 2 to 30, more preferably 3 to 20 and very preferably 3 to 16, compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present application and in the following examples, the structures of the liquid-crystal compounds are indicated by means of acronyms, where the transformation into chemical formulae is carried out in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| $nOCF_3$ | $C_nH_{2n+1}$ | $OCF_3$ | H | H |
| $nOCF_3$.F | $C_nH_{2n+1}$ | $OCF_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Suitable mixture components can be found in Tables A and B.

TABLE A

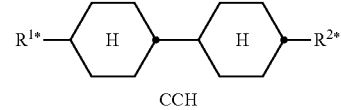

CCH

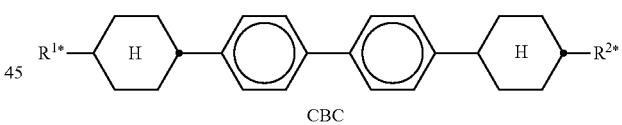

CBC

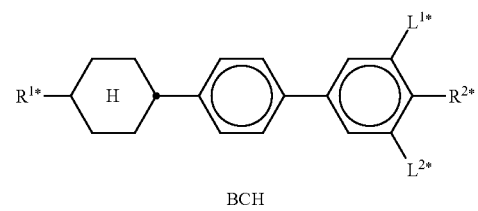

BCH

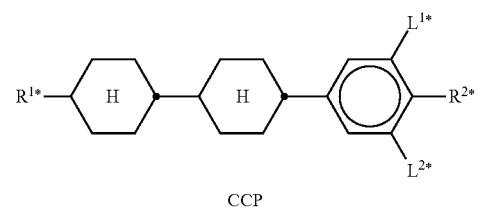

CCP

TABLE A-continued
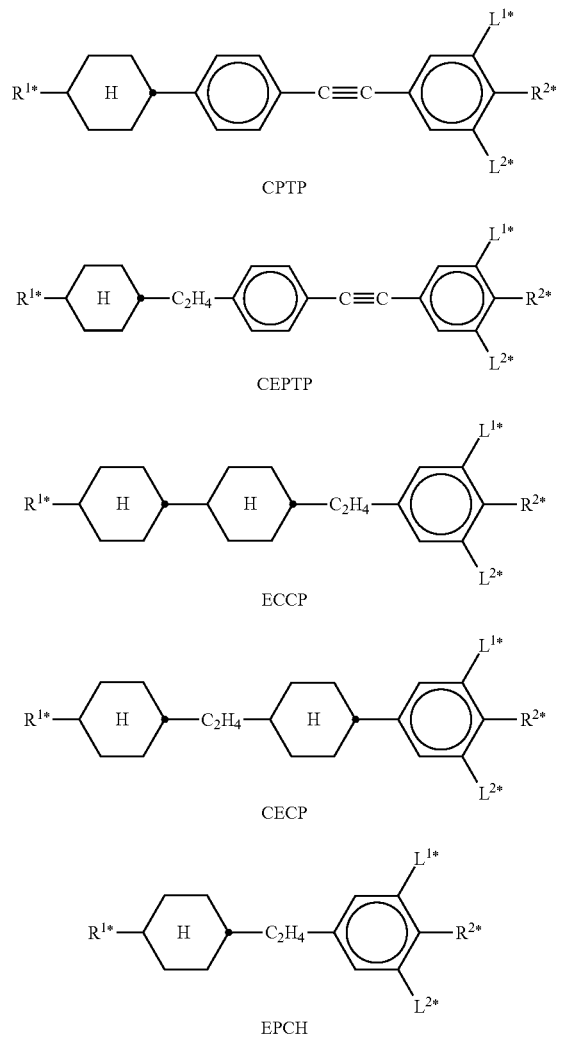
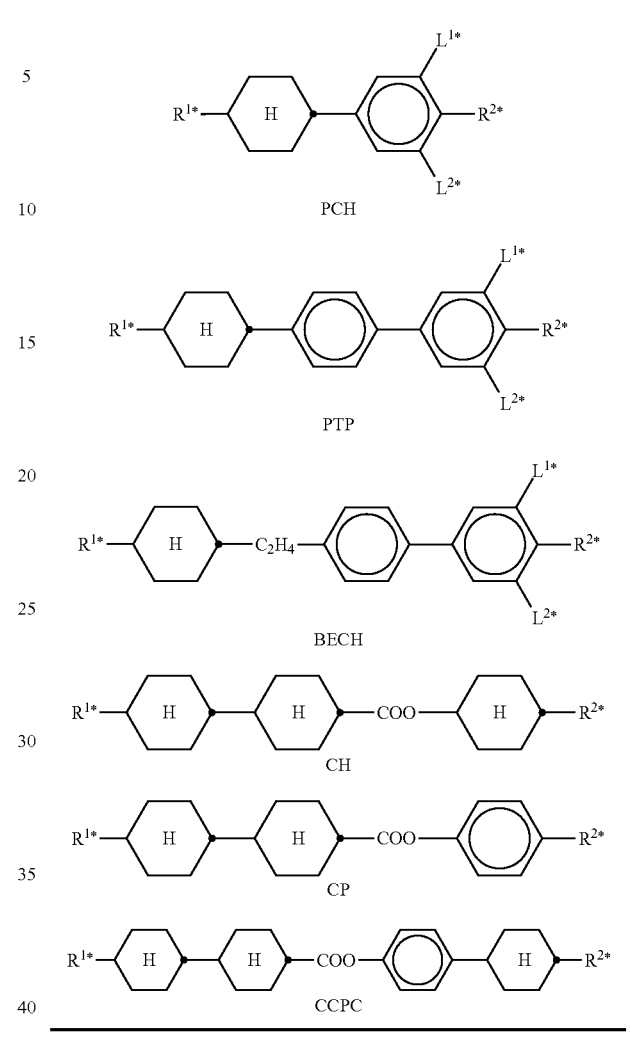
TABLE B
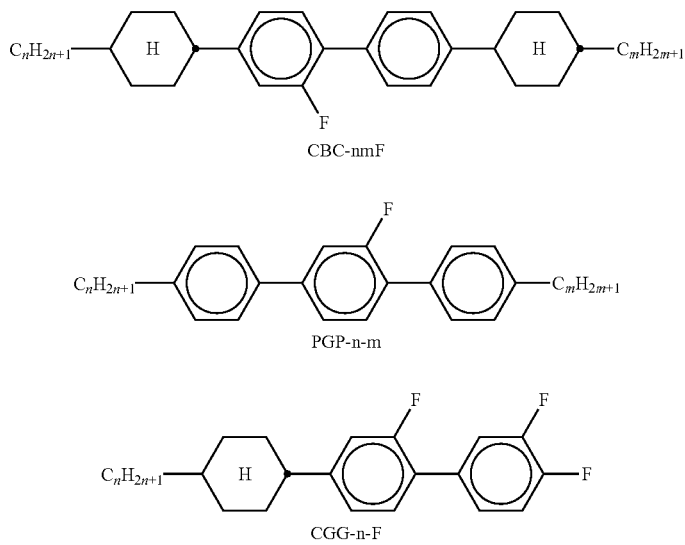

TABLE B-continued

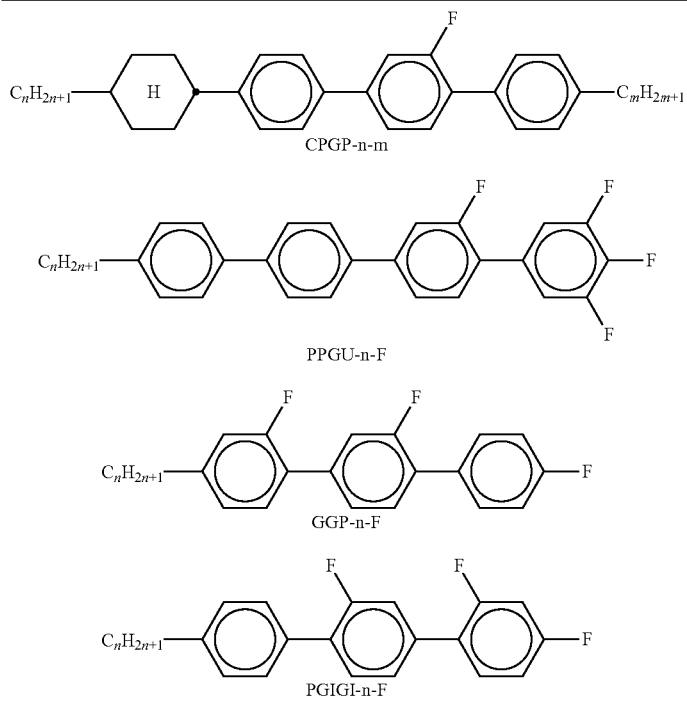

CPGP-n-m

PPGU-n-F

GGP-n-F

PGIGI-n-F

The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

In the present application, unless expressly indicated otherwise, the plural form of a term denotes both the singular form and the plural form, and vice versa. Further combinations of the embodiments and variants of the invention in accordance with the description also arise from the attached claims.

Abbreviations Used:
BuLi n-butyllithium
THF tetrahydrofuran
MTB methyl tert-butyl ether
$SiO_2$ silica gel
RT room temperature (ca. 20° C.)
methoxy-9-BBN B-methoxy-9-borabicyclo[3.3.1]nonane

EXAMPLES

The acetylenes and boronic acids employed are commercially available or can be prepared analogously to known syntheses which are known to the person skilled in the art. The radicals "$C_4H_9$" stand for unbranched n-butyl radicals. The corresponding situation applies to $C_3H_7$, $C_5H_{11}$, $C_6H_{13}$, etc.

1. Synthesis Example 1: Synthesis of 1-(4-n-butyl-phenylethynyl)-2-methyl-4-propyn-1-ylbenzene (corresponds to 4-n-butylphenyl(2-methyl-4-propyn-1-ylphenyl)ethyne)

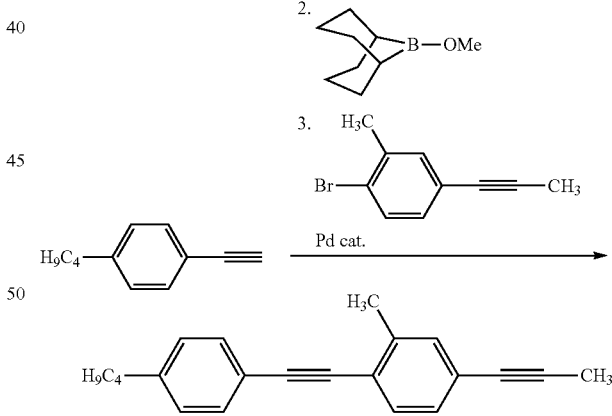

1.1 Steps 1.1 and 1.2

6.8 g of 1-butyl-4-ethynylbenzene in 300 ml of THF are introduced into a 1 l apparatus which has been rendered inert with $N_2$, and the mixture is cooled to −78° C. 41 ml of a 1M solution of lithium bis(trimethylsilyl)amide in n-hexane are added dropwise to this solution, and the mixture is stirred at −78° C. for 30 min. A clear, yellowish reaction mixture forms. 41 ml of a 1M solution of 9-methoxy-9-BBN are then added dropwise. A somewhat darker (pale-orange), clear reaction mixture forms. This is subsequently stirred at −78° C. for 40 min.

1.2 Step 1.3

6.3 g of 1-bromo-2-methyl-4-prop-1-ynylbenzene in 400 ml of THF are introduced into a further apparatus which has been rendered inert with $N_2$, and the catalyst, bis(tricyclohexylphosphine)palladium(II) chloride, is added. The reaction mixture from the first step is then slowly added dropwise at RT. The mixture is subsequently heated under reflux for 12 hours with stirring.

The mixture is subsequently subjected to conventional work-up. In detail, the mixture is cooled to RT, water and MTB are added, and the organic phase is extracted, washed and dried using sodium sulfate, giving a reddish-brown material as crude product. This is eluted over silica gel with heptane. The viscous liquid obtained in this way is crystallised twice from 15 times the amount of pentane at −40° C., giving the product

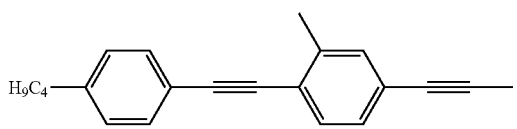

in the form of yellowish crystals. The purity of the product is determined both by means of GC (99.4%) and also by means of HPLC (99.5%). The product is identified by means of mass spectrometry and NMR, and its physical properties are investigated. These are as follows:

C 39 I; $\Delta\varepsilon=+1.6$; $\Delta n=0.360$ and $\gamma_1=223$ mPa·s.

2. Synthesis Example 2: Synthesis of 1-(4-n-butylphenylethynyl)-3-methyl-4-propyn-1-ylbenzene (corresponds to 4-n-butylphenyl-(3-methyl-4-propyn-1-ylphenyl)ethyne)

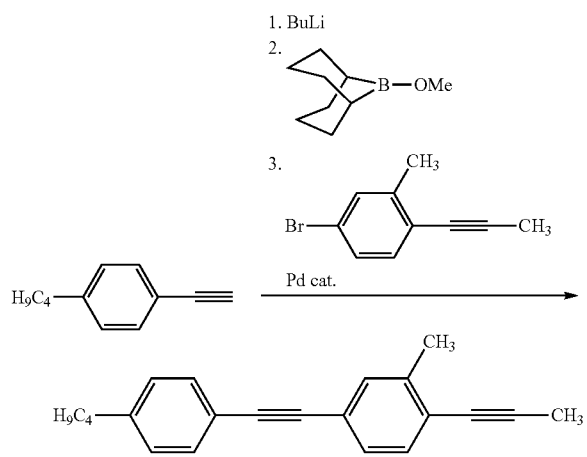

The product from step 1.2 of Example 1 is, as described in step 1.3, added to a solution of 1-bromo-3-methyl-4-prop-1-ynylbenzene. Reaction and work-up of the reaction mixture gives the product

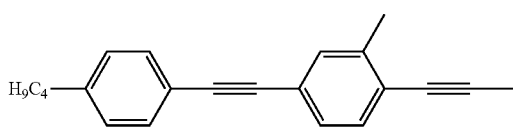

$T_g$ −58 C 24 N (−23.2) I; $\Delta\varepsilon=1.4$; $\Delta n=0.347$ and $\gamma_1=166$ mPa·s.

3. Comparative Synthesis Example 1: Synthesis of 1-(4-n-butylphenylethynyl)-2,3-dimethyl-4-propyn-1-ylbenzene (corresponds to 4-n-butylphenyl-(2,3-dimethyl-4-propyn-1-ylphenyl)ethyne)

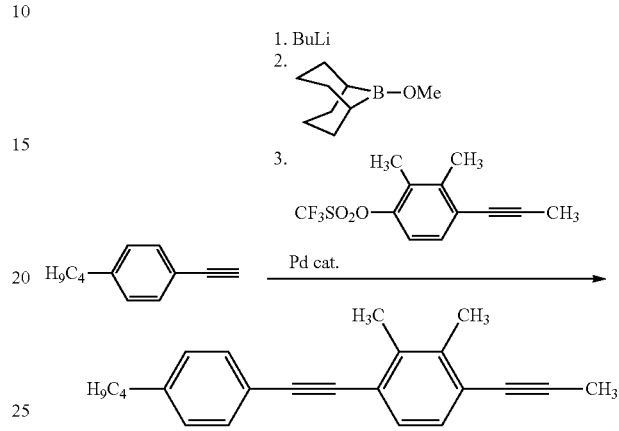

The product from step 1.2 of Example 1 is, as described in step 1.3, added to a solution of 1-bromo-2,3-dimethyl-4-prop-1-ynylbenzene. Reaction and work-up of the reaction mixture gives the product

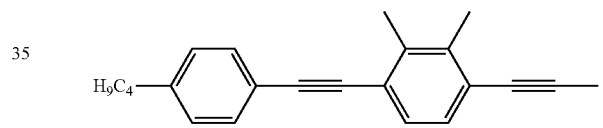

C 72 N (51) I; $\Delta\varepsilon=2.6$; $\Delta n=0.350$ and $\gamma_1=224$ mPa·s.

4. Synthesis Example 3: Synthesis of 1-(4-n-but-1-yn-1-ylphenylethynyl)-2,3-dimethyl-4-propyn-1-ylbenzene (corresponds to 4-n-but-1-yn-1-ylphenyl (2,3-dimethyl-4-propyn-1-ylphenyl)ethyne)

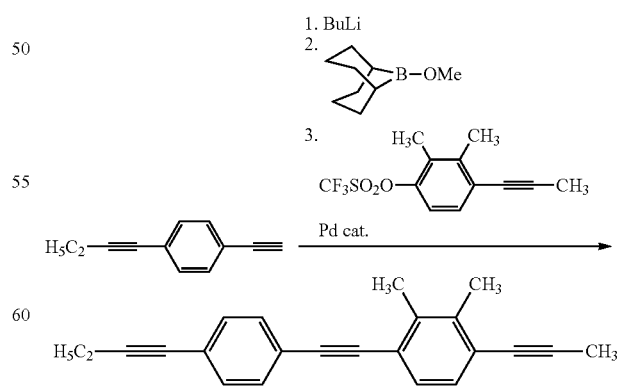

The reaction is carried out analogously to that described in Example 1. Reaction and work-up of the reaction mixture gives the product C 119 N 127.7 I; Δε=2.3; Δn=0.494 and $\gamma_1$=610 mPa·s.

The following are synthesised analogously or in a comparable manner:

5. Substance Example 4

C 22 I; Δε=0.5; Δn=0.408 and $\gamma_1$=482 mPa·s.

6. Substance Example 5

$T_g$ −52 I; Δε=0.7; Δn=0.270 and $\gamma_1$=356 mPa·s.

7. Substance Example 6

C 87 I; Δε=1.8; Δn=0.350 and $\gamma_1$=108 mPa·s.

Mixture Examples

Mixture Example 1

A liquid-crystal medium M-1 having the composition and properties as indicated in the following table is prepared. Compound (1) (No. 15) originates from Synthesis Example 1.

| No. | Composition Compound Abbreviation | |
|---|---|---|
| 1 | BCH-3F.F | 10.8% |
| 2 | BCH-5F.F | 9.0% |
| 3 | ECCP-30CF3 | 4.5% |
| 4 | ECCP-50CF3 | 4.5% |
| 5 | CBC-33F | 1.8% |
| 6 | CBC-53F | 1.8% |
| 7 | CBC-55F | 1.8% |
| 8 | PCH-6F | 7.2% |
| 9 | PCH-7F | 5.4% |
| 10 | CCP-20CF3 | 7.2% |
| 11 | CCP-30CF3 | 10.8% |
| 12 | CCP-40CF3 | 6.3% |
| 13 | CCP-50CF3 | 9.9% |
| 14 | PCH-5F | 9.0% |
| 15 | (1) | 10.0% |
| Σ | | 100.0% |

| Physical properties |
|---|
| T (N, I) = 90.2° C. |
| Δn (20° C., 589.3 nm) = 0.123 |
| Δε (20° C., 1 kHz) = 4.8 |
| $\gamma_1$ (20° C.) = 139 mPa · s |

This mixture is used for applications in the microwave region, in particular for phase shifters or for 'phased-array' antennae.

For comparison, a medium CM-0 without component (1) is prepared from compound Nos. 1-14 of medium M-1, where compound Nos. 1-14 are present in the same relative amounts.

Mixture Examples 2 to 6 and Comparative Mixture Example 0

Liquid-crystal media M-2 to M-6 having the composition of M-1 are prepared, with the difference that, for M-2, compound (2) from Synthesis Example 2 is employed instead of compound (1) and for M-3, compound (3) from Synthesis Example 3 is employed instead of compound (1), etc.

The results for the mixture examples are shown in the following table.

TABLE 1

General physical properties of the mixtures

| Mixture | T (N, I)/° C. | Δn | Δε | $\gamma_1$/mPa · s |
|---|---|---|---|---|
| M-1 | 90.2 | 0.123 | 4.8 | 139 |
| M-2 | 88.8 | 0.122 | 4.8 | 137 |
| M-3 | 100.2 | 0.137 | 5.0 | 153 |
| M-4 | 83.1 | 0.127 | 4.7 | 150 |
| M-5 | 85.3 | 0.114 | 4.8 | 139 |
| M-6 | 90.0 | 0.122 | 5.0 | 129 |
| CM-0 | 92.0 | 0.097 | 5.2 | t.b.d. | t.b.d.: to be determined

TABLE 2

Properties of the mixtures at 19 GHz (20° C.)

| Mixture | $\varepsilon_{r,\parallel}$ | $\varepsilon_{r,\perp}$ | τ | tan $\delta_{\varepsilon,r,\parallel}$ | tan $\delta_{\varepsilon,r,\perp}$ | η |
|---|---|---|---|---|---|---|
| M-1 | 2.63 | 2.29 | 0.131 | 0.0046 | 0.0118 | 11.3 |
| M-2 | 2.56 | 2.26 | 0.118 | 0.0044 | 0.0118 | 10.0 |
| M-3 | 2.68 | 2.32 | 0.135 | 0.0046 | 0.0120 | 11.3 |
| M-4 | t.b.d. | t.b.d. | t.b.d. | t.b.d. | t.b.d. | t.b.d. |

TABLE 2-continued

Properties of the mixtures at 19 GHz (20° C.)

| Mixture | $\varepsilon_{r,\parallel}$ | $\varepsilon_{r,\perp}$ | $\tau$ | $\tan \delta_{\varepsilon,r,\parallel}$ | $\tan \delta_{\varepsilon,r,\perp}$ | $\eta$ |
|---|---|---|---|---|---|---|
| M-5 | t.b.d. | t.b.d. | t.b.d. | t.b.d. | t.b.d. | t.b.d. |
| M-6 | t.b.d. | t.b.d. | t.b.d. | t.b.d. | t.b.d. | t.b.d. |
| CM-0 | 2.56 | 2.29 | 0.107 | 0.0049 | 0.0126 | 8.50 |

$\tau$ = tunability;
$\eta$ = material quality;
$\tan \delta_{\varepsilon,r}$ = dielectric loss factors,
t.b.d.: to be determined The tunability $\tau$ and the material quality $\eta$ are significantly improved for mixtures M-1 to M-3 compared with comparative mixture CM-0 and comparative mixture CM-1.

The results and the comparison with base mixture CM-0 are shown in Table 1. Compared with base mixture CM 0, both significantly increased tunability, and also better material quality are evident.

The invention claimed is:

1. A compound of formula I

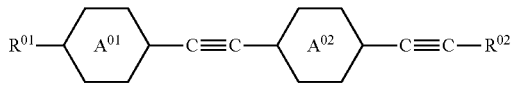

in which

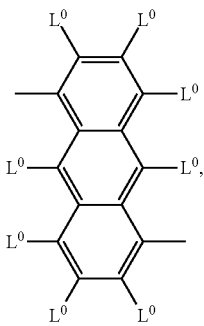 denotes 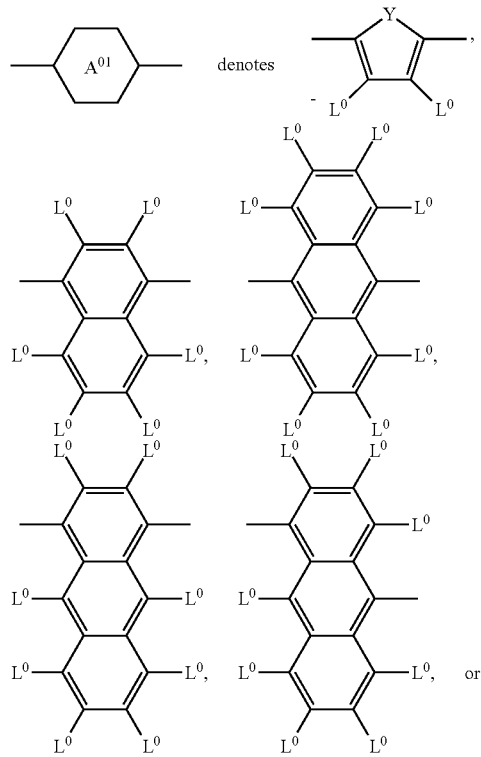

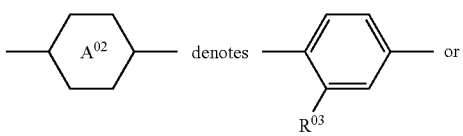

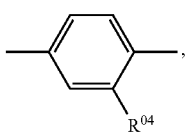

where in the 1,4-phenylene groups, one C—H group or two C—H groups are optionally replaced by N, Y denotes S or O, $L^0$ on each occurrence, independently of one another, denotes H, Br, Cl, F, —CN, —NCS, —SCN, $SF_5$, $C_1$-$C_{10}$ alkyl, $C_1$-$C_{10}$ alkoxy, $C_3$-$C_6$ cycloalkyl or a mono- or polyfluorinated $C_1$-$C_{10}$ alkyl or alkoxy group, $R^{01}$ and $R^{02}$ each, independently of one another, denote a halogenated or unsubstituted alkyl radical having 1 to 15 C atoms, in which one or more $CH_2$ groups are optionally replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another, and $R^{01}$ also denotes ethynyl, and $R^{03}$ and $R^{04}$ each, independently of one another, denote a halogenated or unsubstituted alkyl radical having 1 to 6 C atoms, in which one or more $CH_2$ groups are optionally replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another.

2. The compound according to claim 1, wherein

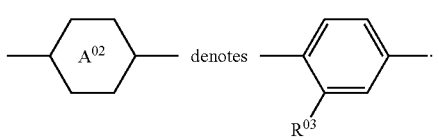

3. The compound according to claim 1, wherein

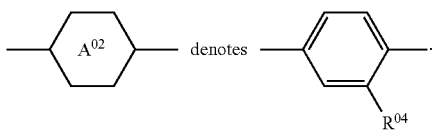

4. The compound according to claim 1, wherein

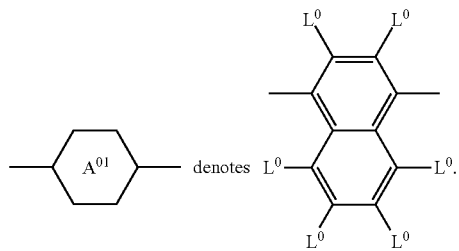

5. The compound according to claim 1, wherein $R^{01}$ denotes alk-1-ynyl.

6. A liquid-crystal medium, comprising one or more compounds of formula I according to claim 1.

7. The liquid-crystal medium according to claim 6, further comprising one or more compounds of formula II:

$$L^{11}\text{-}(A^{11})\text{-}Z^{11}\text{-}_p(A^{12})\text{-}Z^{12}\text{-}(A^{13})\text{-}Z^{13}\text{-}(A^{14})\text{-}_q L^{12}$$  II in which:

$L^{11}$ denotes $R^{11}$ or $X^{11}$, $L^{12}$ denotes $R^{12}$ or $X^{12}$, $R^{11}$ and $R^{12}$, independently of one another, denote unfluorinated alkyl or unfluorinated alkoxy having 1 to 17 C atoms or unfluorinated alkenyl, unfluorinated alkynyl, unfluorinated alkenyloxy or unfluorinated alkoxyalkyl having 2 to 15 C atoms, $X^{11}$ and $X^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, p, q independently denote 0 or 1, $Z^{11}$ to $Z^{13}$, independently of one another, denote trans-CH=CH—, trans-CF=CF—, —C≡C— or a single bond,

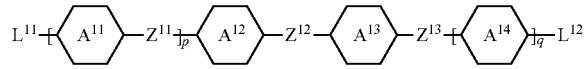

independently of one another, denote

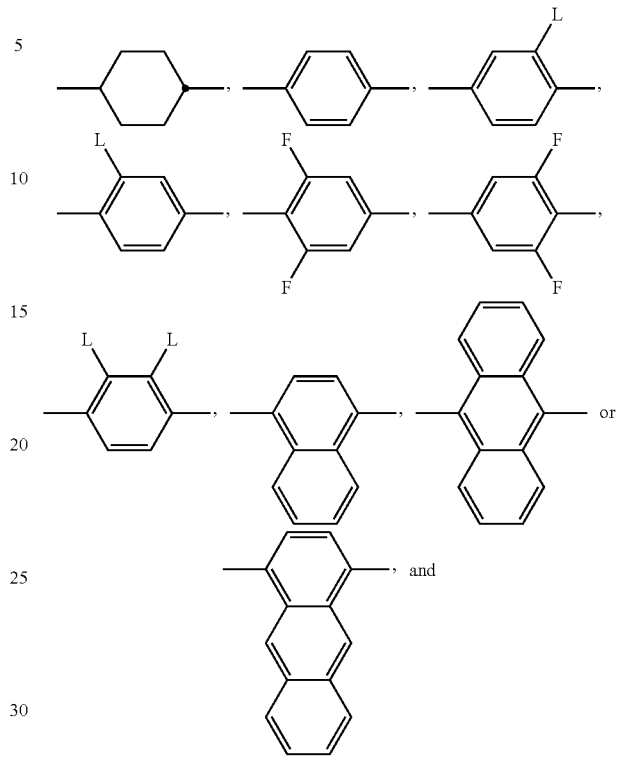

L on each occurrence, independently of one another, denotes branched or unbranched alkyl, alkenyl or alkynyl having 1 to 12 C atoms, in which one or more —CH$_2$— groups are, independently of one another, optionally replaced by O, or denotes $C_3$-$C_6$ cycloalkyl, $C_3$-$C_6$ cycloalkenyl, fluorinated alkyl or alkenyl, fluorinated alkoxy or alkenyloxy, F, Cl, Br, CN, NCS, SCN or SF$_5$.

8. The liquid-crystal medium according to claim 6, wherein the concentration of the one or more compounds of formula I in the medium is in total 5% to 95%.

9. A process for preparing the liquid-crystal medium according to claim 6, comprising mixing the one or more compounds of formula I with one or more further compounds and optionally with one or more additives.

10. A component for high-frequency technology, comprising a liquid-crystal medium according to claim 6.

11. The component according to claim 10, which is a phase shifter or a plurality of functionally connected phase shifters.

12. A phased-array antenna, which comprises one or more components according to claim 10.

13. The compound according to claim 1, wherein $R^{03}$ and $R^{04}$ each, independently of one another, denote a halogenated or unsubstituted alkyl radical having 1, 2 or 3 C atoms, in which one or more CH$_2$ groups are optionally replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another.

14. The compound according to claim 1, wherein $R^{02}$ denotes a propyl, butyl, pentyl or hexyl radical.

15. The compound according to claim 4, which is

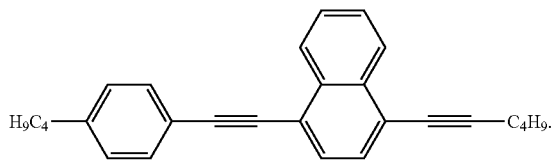

16. A liquid-crystal medium, comprising one or more compounds according to claim 4.

17. The liquid-crystal medium according to claim 16, further comprising one or more compounds of formula II:

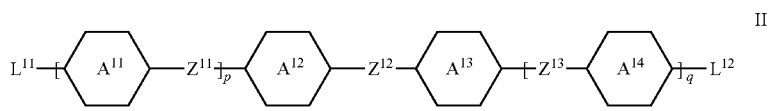

in which:

L$^{11}$ denotes R$^{11}$ or X$^1$,

L$^{12}$ denotes R$^{12}$ or X$^{12}$,

R$^{11}$ and R$^{12}$, independently of one another, denote unfluorinated alkyl or unfluorinated alkoxy having 1 to 17 C atoms or unfluorinated alkenyl, unfluorinated alkynyl, unfluorinated alkenyloxy or unfluorinated alkoxyalkyl having 2 to 15 C atoms, X$^{11}$ and X$^{12}$, independently of one another, denote F, Cl, Br, —CN, —NCS, —SCN, —SF$_5$, fluorinated alkyl or fluorinated alkoxy having 1 to 7 C atoms or fluorinated alkenyl, fluorinated alkenyloxy or fluorinated alkoxyalkyl having 2 to 7 C atoms, p, q independently denote 0 or 1, Z$^{11}$ to Z$^{13}$, independently of one another, denote trans-CH=CH—, trans-CF=CF—, —C≡C— or a single bond,

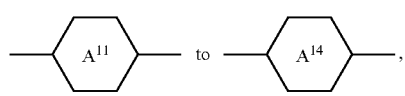

independently of one another, denote

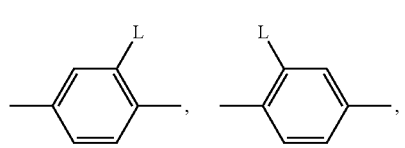

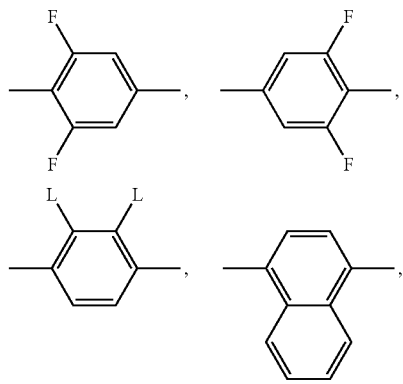

and

L on each occurrence, independently of one another, denotes branched or unbranched alkyl, alkenyl or alkynyl having 1 to 12 C atoms, in which one or more —CH$_2$— groups are, independently of one another, optionally replaced by O, or denotes C$_3$-C$_6$ cycloalkyl, C$_3$-C$_6$ cycloalkenyl, fluorinated alkyl or alkenyl, fluorinated alkoxy or alkenyloxy, F, Cl, Br, CN, NCS, SCN or SF$_5$.

18. The liquid-crystal medium according to claim 16, wherein the concentration of the one or more compounds of formula I in the medium is in total 5% to 95%.

19. A component for high-frequency technology, comprising a liquid-crystal medium according to claim 16, and which is a phase shifter or a plurality of functionally connected phase shifters.

20. A phased-array antenna, which comprises one or more components according to claim 19.

21. A compound of formula I

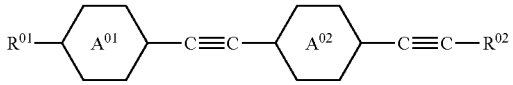

in which

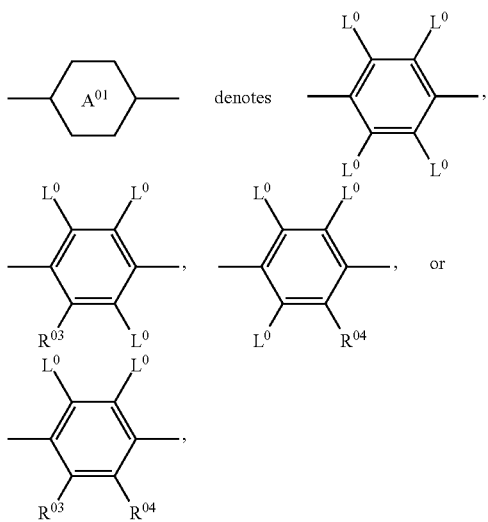

where in the 1,4-phenylene groups, one C—H group or two C—H groups are replaced by N, which one C—H group or two C—H groups are present as a result of $L^0$ being H on the carbon atom of said one C—H group or two C—H groups,

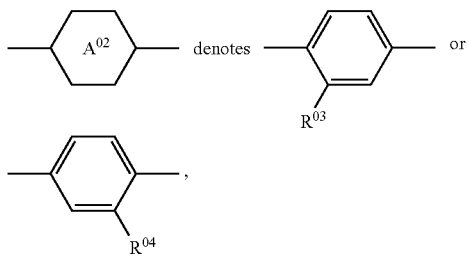

where in the 1,4-phenylene groups, one C—H group or two C—H groups are optionally replaced by N, $L^0$ on each occurrence, independently of one another, denotes H, Br, Cl, F, —CN, —NCS, —SCN, $SF_5$, $C_1$-$C_{10}$ alkyl, $C_1$-$C_{10}$ alkoxy, $C_3$-$C_6$ cycloalkyl or a mono- or polyfluorinated $C_1$-$C_{10}$ alkyl or alkoxy group, $R^{01}$ and $R^{02}$ each, independently of one another, denote a halogenated or unsubstituted alkyl radical having 1 to 15 C atoms, in which one or more $CH_2$ groups are optionally replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another, and $R^{01}$ also denotes ethynyl, and $R^{03}$ and $R^{04}$ each, independently of one another, denote a halogenated or unsubstituted alkyl radical having 1 to 6 C atoms, in which one or more $CH_2$ groups are optionally replaced, independently of one another, by —C≡C—, —CH=CH—, —CF=CF—, —CF=CH—, —CH=CF—, —(CO)O—, —O(CO)—, —(CO)—, —O— or —S— in such a way that O or S atoms are not linked directly to one another.

22. The compound according to claim 1, wherein

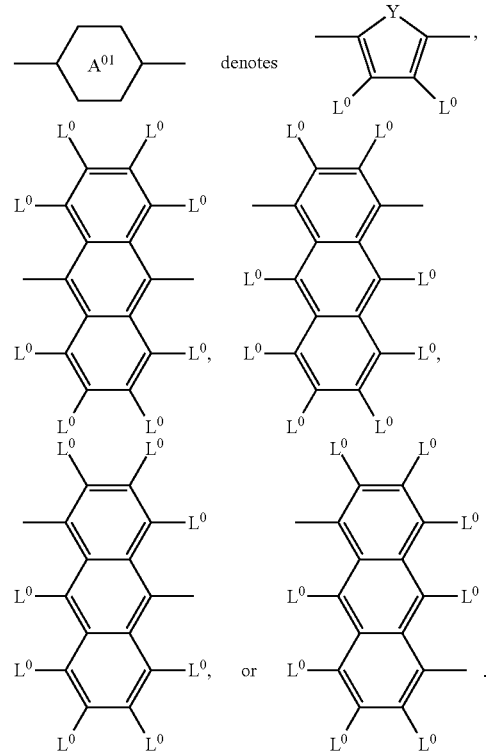

* * * * *